United States Patent [19]

Mueller

[11] 4,305,276
[45] Dec. 15, 1981

[54] TEMPERATURE CONTROLLED OVEN CHAMBER FOR GAS CHROMATOGRAPHY

[75] Inventor: Friedhelm Mueller, Linkenhelm-Hochstetten, Fed. Rep. of Germany

[73] Assignee: Siemens Aktiengesellschaft, Berlin and Munich, Fed. Rep. of Germany

[21] Appl. No.: 153,885

[22] Filed: May 27, 1980

[30] Foreign Application Priority Data

May 25, 1979 [DE] Fed. Rep. of Germany ....... 2921358

[51] Int. Cl.³ ........................................... G01N 31/08
[52] U.S. Cl. ..................................................... 73/23.1
[58] Field of Search ............... 73/23.1, 61.1 C; 55/67, 55/197; 432/250, 266

[56] References Cited

U.S. PATENT DOCUMENTS 3,385,099  5/1968  Diem et al. ........................... 73/23.1

FOREIGN PATENT DOCUMENTS 1181448  11/1964  Fed. Rep. of Germany .

Primary Examiner—Jerry W. Myracle
Attorney, Agent, or Firm—Spellman, Joel & Pelton

[57] ABSTRACT

A temperature controlled oven chamber for gas chromatography incorporates a first stationary chamber wall, a second stationary chamber wall arranged remote from the first wall, and a displaceable chamber wall which is moveable between a closed position and an open position. In the closed position, the displaceable chamber wall forms the casing of the chamber or housing, and surrounds stationary analytical devices. In the open position, the displaceable wall is moved away from the first stationary wall, thereby opening the chamber or housing and yielding access to the analytical devices. When moving from the closed position to the open position, the displaceable wall will enclose the second wall at least temporarily.

15 Claims, 2 Drawing Figures

TEMPERATURE CONTROLLED OVEN CHAMBER FOR GAS CHROMATOGRAPHY

BACKGROUND OF THE INVENTION

1. Field of the Invention

This invention relates to an oven for gas chromatography. In particular, this invention relates to a temperature controlled oven chamber for gas chromatography, whereby the chamber is made of heat insulating walls and contains stationary analytical devices such as a chromatographic column, an air circulating device and a heating device for keeping said column at a desired temperature.

2. Description of the Prior Art

It is known that the analytical devices of a gas chromatograph, such as separation columns, column switching devices, injectors or parts thereof, detectors and change-over valves, have to be maintained at temperatures which are critically constant. For this purpose, particularly the separating columns, but also other parts are disposed in a heat insulating chamber the interior of which is maintained at a predetermined temperature by means of controllable heating and air circulating devices.

In gas chromatography, especially in laboratories, the separating columns have to be changed frequently. Therefore, a good accessibility of the analytical devices is mandatory, particularly when sensitive glass capillary columns and assemblies of interconnected separation columns are used.

It is for this reason that a known version of temperature controlled oven chambers is designed like a warming cabinet having a hinged side panel which can be opened to expose the interior. The stationary analytical devices along with their electric and pneumatic connections are arranged in the interior of the cabinet, and they can easily be connected to external systems, for instance to a mass spectrometer which is to be coupled at the outlet side of the gas chromatograph. A disadvantage of this oven chamber is its poor accessibility through the hinged opening. In addition, there is a hazard of burning for the operating personnel when changes of analytical devices shall be made after an antecedant operation.

In order to improve the accessibility, in another version of temperature controlled oven chambers, the analytical devices are arranged in or on the chamber top which is guided by a column and which can be lifted upward away from the oven chamber or housing. When the chamber top is lifted, the analytical devices are well accessible and there is no danger of burning. However, the electrical and pneumatical connection and supply lines must be flexible and adequately long. This reduces the possibility for coupling with external systems which require short and heated connection lines. Another disadvantage of such a design resides in the fact that a misadjustment of sensitive measuring systems may occur due to a movement of the analytical devices.

The German Auslegeschrift No. 1,181,448 discloses an oven for gas chromatography which has an open and a closed operational position. The oven has the shape of a cylindrical pot. In the closed position, the pot which contains an electric heater is turned upside down over the chromatographic column. The internal temperature of the oven is controlled in order to achieve a value which is of advantage with regard to the chromatographic separation of the substance under examination. A fan which is driven by an electric motor circulates the air inside the pot. After an analysis of the substance under examination has taken place, the pot can be moved upward. In one version of the known oven (see FIG. 1), the pot can completely be removed from the chromatographic column. In this open position, the operator of the oven has free access to the chromatographic column. In this position, the column can cool down quickly, and the column can easily be exchanged. Yet, the known oven has to be disassembled when access to the interior of the oven chamber is necessary or desired. This is a certain disadvantage, in particular since the cylindric pot contains the heater which has to be handled particularly carefully. The hot top part of the oven has to be laid down somewhere, so that some space for this purpose is required. In addition, there is a certain hazard that the column is inadvertently touched or even damaged when the protecting top part of the oven is removed.

SUMMARY OF THE INVENTION

1. Objects

It is an object of this invention to provide an oven chamber for gas chromatography which is sealed in a heat-tight manner in its closing position and which yields free accessibility to its analytic devices in its open position.

It is another object of this invention to provide an oven chamber for gas chromatography which has a minimized hazard with regard to burning the operator when handling analytic devices within the chamber.

It is still another object of this invention to provide an oven chamber for gas chromatography in which the connection and supply lines between analytic devices within the chamber and external systems can be chosen to be short.

It is still another object of this invention to provide an oven chamber for gas chromatography which has not to be disassembled in order to yield access to its chromatographic column and its other internal analytical devices.

It is still another object of this invention to provide an oven chamber for gas chromatography which makes access to the inner parts and devices very easy and which minimizes the risk of damage when the chamber is opened.

It is still another object of the invention to provide an oven chamber for gas chromatography which can be opened and closed and the analytic devices of which are accessible at least from three directions.

2. Summary

According to this invention, a temperature controlled oven chamber for gas chromatography incorporates, in combination, a first stationary chamber wall, a second stationary chamber wall arranged remote from the first wall, and a displaceable chamber wall which is moveable between a closed position and an open position. In the closed position, the displaceable chamber wall forms the casing of the chamber or housing, and surrounds the stationary analytical devices. In the open position, the displaceable wall is moved away from the first stationary wall, thereby opening the chamber or housing and yielding access to the analytical devices.

The displaceable chamber wall may have an axis of symmetry. For instance, this wall may be formed by a cylindric casing, such as a tubular piece, or a rectangular casing comprising four walls. The displaceable chamber wall is moveable along the axis of symmetry.

In a preferred embodiment of the invention, the first stationary wall is an upper end face of a housing, and the analytical devices are arranged in or on this upper end face. The second wall is the lower end face of the housing. This lower end face is supported by a stationary base. The base may also support or hold a heating and air circulating device. The displaceable wall means are moveable along the outside of the stationary base in a telescopic manner from the open position to the closed position, and vice versa.

In an oven chamber according to the invention, the analytical devices are well accessible from various directions. In the preferred embodiment, the stationary analytical devices are arranged in or on the upper end face, whereby all connections are made with short pneumatic and electrical connection lines. The connection of or to external systems does not pose any problems.

The foregoing and other objects, features and advantages of the invention will be apparent from the following more particular description of preferred embodiments of the invention as illustrated in the accompanying drawings.

BRIEF DESCRIPTION OF THE DRAWINGS

In the drawings.

Like numerals refer to like parts and elements throughout the drawings.

DETAILED DESCRIPTION OF THE PREFERRED EMBODIMENTS

Figure 1:
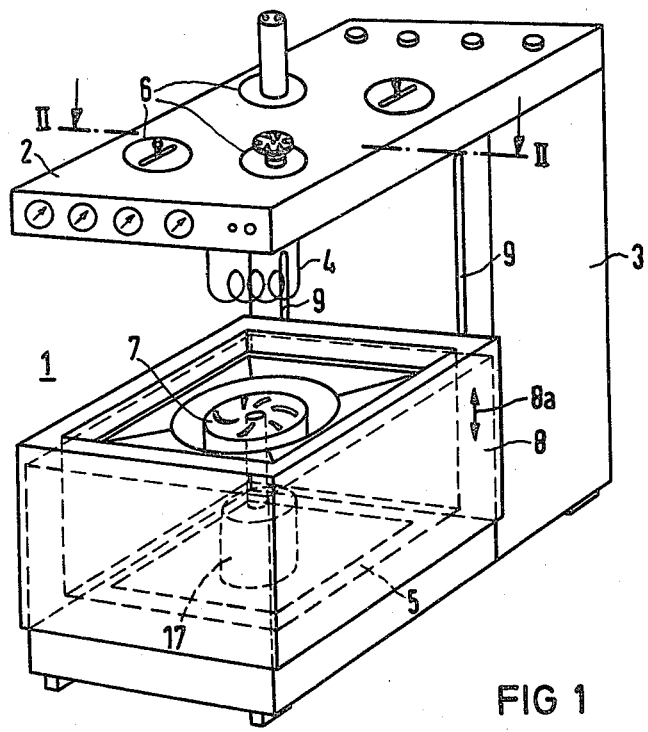
FIG. 1 is a perspective view of a temperature controlled oven chamber for gas chromatography according to the invention, the chamber being in its open position.

With reference to FIG. 1, a temperature controlled or stabilized oven for gas chromatography is shown. The oven contains a housing or chamber 1 having an upper end face, a lower end face and four heat insulating side walls in the form of a parallelepiped block. The upper end face of the chamber 1 is formed by an upper heat insulating plate 2 which is firmly connected to a cantilever 3 arranged outside the housing 1. Located in and on the upper plate 2 are analytical devices 4 in an easily accessible manner. The analytical devices 4, such as separation columns, and injectors (not shown), detectors (not shown), switch valves (not shown), as well as accessory devices necessary for the operation of the analytical devices, such as connections, terminals and operation and control elements 6, are disposed in or on the plate 2 in a fixed position.

A stationary support or base 5 contains a driving motor 17 for driving a controllable heating and air circulating device 7. This device 7 is arranged above a heat insulating lower plate 2' (see FIG. 2) of the housing 1. The lower plate 2' is connected to the upper end of the stationary base 5.

The four heat insulating side faces form a rectangular casing 8. The casing 8 may be lowered or lifted vertically along the stationary base 5 in a telescopic manner. This is indicated by a double arrow 8a. The direction of movement is parallel to the axis of symmetry of the casing 8.

After a work has been done the analytical devices 4, the casing 8 may be moved from the open position (shown in FIG. 1) upwardly to a closed position, wherein the casing 8 is sealed in a heat tight manner against the lower plate 2'. The mechanism for lifting the casinhg 8 along two guide rails 9 may be any well known power means such as an electric motor (not shown) which is housed in the cantilever 3.

Figure 2:
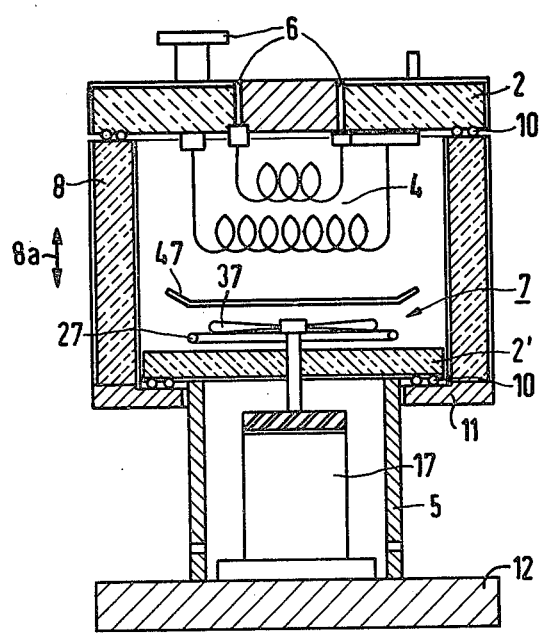
FIG. 2 is a longitudinal cross-sectional view of the oven chamber through II—II of FIG. 1 and in its closed position.

In FIG. 2, the oven chamber 1 is shown in its closed position. Heat insulating seals or packings 10 are provided in the gaps between the upper end faces of the casing 8 and the lower end face of the upper plate 2. Heat insulating seals or packings 10 are also provided between the lower end face of the lower plate 2' and the upper part of a rectangular frame 11 which is connected to the lower end of the casing 8. The frame 11 partially overlaps the lower plate 2' in order to provide for a sealing rim.

The dimensions of the stationary base 5 and the frame 11 are such that the casing 8 may slide therealong when the oven is opened.

As can be seen in FIG. 2, the driving motor 17 for driving the heating and air circulating device 7 is arranged outside the chamber 1 in a cool chamber, in the base 5. The heating and air circulating device 7 in the chamber 1 contains a heating coil 27, a fan 37 and an air conducting sheet 47. The axis of the motor 7 extends in a vertical direction through the lower plate 2'.

The stationary base 5 is supported by a horizontal supporting plate 12 which is connected to the cantilever 3.

The temperature controlled gas chromatographic oven illustrated in FIGS. 1 and 2 represents a compact unit. In the open position, the operator of the oven has free access to the column and othr analytical devices 4 from three directions. Another advantage resides in the fact that in the open position the chromatographic column as well as the other analytical devices 4 and the device 7 are protected to a large extent from any inadvertant contact by the operator.

While the form of the oven chambers for gas chromatography herein described constitute preferred embodiments of the invention, it is to be understood that the invention is not limited to these precise forms of assembly and that a variety of changes may be made therein without departing from the scope of the invention.

What is claimed is:

1. A temperature controlled oven chamber for gas chromatography, said chamber containing stationary analytical devices including a chromatographic column, an air circulating device and a heating device for maintaining said column at a desired temperature, the improvement comprising, in combination:
   (a) first stationary chamber wall means;
   (b) second stationary chamber wall means arranged remote from said first wall means; and
   (c) displaceable chamber wall means moveable between
     ($\alpha$) a closed position, in which said displaceable wall means are in contact with said first and second stationary wall means, thereby closing said oven chamber and insulating said analtyical devices from the outside; and
     ($\beta$) an open position, in which said displaceable wall means are remote from said first wall means and shifted towards said second wall means, thereby opening said chamber for access to said analytical devices, said displaceable wall means enclosing said second wall means at least temporarily when moving from said closed position to said open position.

2. The oven chamber of claim 1, wherein said displaceable wall means has an axis of symmetry, and wherein said displaceable wall means is shifted along said axis when moved from said closed position to said open position.

3. The oven chamber of claim 2, wherein said axis is arranged vertically.

4. The oven chamber of claim 2, wherein said displaceable wall means comprise four walls which are arranged rectangularly with respect to each other.

5. The oven chamber of claim 4, wherein said plates are arranged parallel to each other.

6. The oven chamber of claim 1, wherein said first wall means comprise an upper plate, and wherein said second wall means comprise a lower plate.

7. The oven chamber of claim 6, wherein at least one of said plates is part of a cantilever.

8. The oven chamber of claim 6, wherein said analytical devices are arranged on one of said plates.

9. The oven chamber of claim 5, wherein one of said plates is supported by a stationary base, and wherein said displaceable wall means is moveable along the outside of said base in a telescopic manner.

10. The oven chamber of claim 9, wherein a motor for driving said air circulating device is arranged in said base, the axis of said motor extending through said one plate.

11. The oven chamber of claim 9, wherein said stationary base is connected to a horizontal supporting plate, and wherein a vertical member is provided to carry the other one of said plates.

12. The oven chamber of claim 9, wherein said displaceable wall means have a frame on its lower side for sliding on said stationary base.

13. The oven chamber of claim 1, wherein heat sealing means are provided between said first wall means and said displaceable wall means.

14. The oven chamber of claim 1, wherein heat sealing means are provided between said second wall means and said displaceable wall means.

15. A temperature controlled oven chamber for gas chromatography, said chamber containing stationary analytical devices including a chromatographic column, an air circulating device and a heating device for maintaining said column at a desired temperature, said chamber having first and second stationary end walls, said second end wall being substantially parallel to said first end wall, and side walls extending between said end walls, said side walls being slideably moveable longitudinally and axially of said chamber from a heat sealing closed position to an open position, exposing in said open position the interior of said chamber from a front and at least two opposite sides.

* * * * *